United States Patent [19]
Richelsoph

[11] Patent Number: 5,749,916
[45] Date of Patent: May 12, 1998

[54] FUSION IMPLANT

[75] Inventor: Marc Richelsoph, Memphis, Tenn.

[73] Assignee: Spinal Innovations, Memphis, Tenn.

[21] Appl. No.: 786,020

[22] Filed: Jan. 21, 1997

[51] Int. Cl.$^6$ .................................................. A61F 2/44
[52] U.S. Cl. .................................................. 623/17; 606/61
[58] Field of Search .......................... 623/16, 17; 606/60, 606/61

[56] References Cited

U.S. PATENT DOCUMENTS

| | | |
|---|---|---|
| 3,848,601 | 11/1974 | Ma et al. . |
| 3,867,728 | 2/1975 | Stubstad et al. ........................ 623/17 |
| 3,875,595 | 4/1975 | Froning ................................. 623/17 |
| 4,011,602 | 3/1977 | Rybicki et al. . |
| 4,309,777 | 1/1982 | Patil .................................... 623/17 |
| 4,636,217 | 1/1987 | Ogilvie et al. ......................... 623/17 |
| 4,653,481 | 3/1987 | Howland et al. . |
| 4,743,256 | 5/1988 | Brantigan .............................. 623/17 |
| 4,772,287 | 9/1988 | Ray et al. ............................. 623/17 |
| 4,834,757 | 5/1989 | Brantigan .............................. 623/17 |
| 4,840,633 | 6/1989 | Kallabis et al. ....................... 623/23 |
| 4,932,969 | 6/1990 | Frey et al. ............................ 623/17 |
| 4,932,975 | 6/1990 | Mair et al. ............................ 623/17 |
| 4,936,851 | 6/1990 | Fox et al. ............................. 623/16 |
| 4,961,740 | 10/1990 | Ray et al. ............................. 606/61 |
| 5,015,247 | 5/1991 | Michelson ............................. 606/61 |
| 5,026,373 | 6/1991 | Ray et al. ............................. 606/61 |
| 5,055,104 | 10/1991 | Ray ................................... 606/61 |
| 5,059,193 | 10/1991 | Kuslich ............................... 606/61 |
| 5,062,845 | 11/1991 | Kuslich et al. ......................... 606/80 |
| 5,071,437 | 12/1991 | Steffee ................................ 623/17 |
| 5,123,926 | 6/1992 | Pisharodi ........................... 606/61 X |
| 5,171,281 | 12/1992 | Parsons et al. ........................ 623/17 |
| 5,192,327 | 3/1993 | Brantigan .............................. 623/17 |
| 5,263,953 | 11/1993 | Bagby ................................. 606/61 |
| 5,415,661 | 5/1995 | Holmes ................................ 606/69 |
| 5,458,638 | 10/1995 | Kuslich et al. ........................ 623/17 |
| 5,489,308 | 2/1996 | Kuslich et al. ........................ 623/17 |
| 5,517,180 | 5/1996 | Heggeness et al. ..................... 623/17 |
| 5,609,635 | 3/1997 | Michelson ............................ 623/17 |
| 5,609,636 | 3/1997 | Kohrs et al. .......................... 623/17 |

*Primary Examiner*—Mary Beth Jones
*Attorney, Agent, or Firm*—Kohn & Associates

[57] ABSTRACT

A fusion implant for insertion between opposing vertabrae includes a body having an inner surface defining a hollow inner chamber for containing a graft material therein. The body includes a stress transfer mechanism for transferring stress from the vertabrae surrounding the implant to the graft material contained within the implant. A method is provided for implanting the fusion implant between opposing vertabraes by the steps of inserting an implant into a collapsed disc space between adjacent vertabrae, the implant including a collapsed body, and expanding the body to spread the adjacent vertabrae apart.

25 Claims, 3 Drawing Sheets

FUSION IMPLANT

TECHNICAL FIELD

The present invention relates to implants for insertion between opposing vertebrae for stabilizing the spine. More particularly, the present invention provides a fusion cage or body which is surgically implanted to stabilize adjacent vertebrae of the spine while inducing bone growth therebetween.

BACKGROUND OF THE INVENTION

Fusion cages or interbody fusion devices provide a means of opening the collapsed disc space between opposing vertebrae to relieve pressure on nerves and/or the spinal cord by placing a spacer or spacers in the disc space.

Presently used fusion cages are either cylindrical or rectangular devices having an external threaded or toothed portion for engaging the vertebral end plates in order to prevent the cage from slipping. Such cages are generally hollow. They can be filled with graft in order to induce fusion of the two vertebrae together. Such devices provide great potential for eliminating the large incisions required for posterior instrumentation and open a door for minimally invasive surgery.

The art of spinal implant, such as fusion cages has become highly developed. Recent developments have been directed to various aspects of the cage design. For example, the U.S. Pat. No. 5,055,104 to Ray, issued Oct. 9, 1991, provides a method of surgically implanting threaded fusion cages between adjacent lower back vertebrae by an anterior approach. The device disclosed therein consists of a shape-retaining solid helix of wire that is hollow within the helix and has openings between adjacent turns of the cage.

The U.S. Pat. No. 4,011,602 to Rybicki et al. discloses an expandable device for attachment to bone tissue. The device includes an adjustable mechanism for expanding the body member against tissue in which it is implanted to an extent such as to provide a compressive stress capable of maintaining a snug and stable fit. However, once adjusted, the device is solid and fixed, just as the device disclosed in the Ray patent discussed above.

The U.S. Pat. No. 5,489,308 to Kuslich et al., issued Feb. 6, 1996 also provides a spinal implant for use in spinal stabilization. The implant includes holes therethrough which are positioned to chip bone into the implant as the implant is rotated.

Each of the aforementioned patents, as well as many other patents in the art, address such issues as anterior approach, expansion and then fixation, and means for automatically positioning bone chips within the hollow space therein to promote fusion. However, there remains several issues of maximal importance which are not addressed by the prior art.

For example, fusion devices presently in use are cylindrical or rectangular devices which are large and bulky. Size is an extremely important factor in minimally invasive surgery wherein the device is placed inside the body using a cannula to minimize the incision size and therefore hospital recovery time. In this process, it is desirable to use as small of an incision as possible. A cannula is used to track the implant to its desired destination, the implant having to be smaller in size than the inner core of the cannula to allow insertion therethrough. Present spinal implants require a larger incision due to their large and bulky shape necessitated by their structure thereby not being directed at minimizing the incision.

Another problem with presently used implant cages is a complete lack of understanding of load sharing, Wolf's law, and fusion quality. The above cited patents, as well as others, provide a fixed device which is inserted between the vertebral end plates and filled with graft. It has been previously assumed that if the graft is placed properly, fusion will occur. However, bone quality is related to stress. Wolf's law states that bone grows along lines of stress. The aforementioned prior art cages hold the vertebral bodies apart and act merely as solid spacers. Therefore, the graft material inside the cage resorbs and is never stressed. Without stress, the graft material inside the cage does not effectively provide fusion quality. If a fusion takes place, which is difficult to determine at best in metal cages using X-rays or most other diagnostic techniques, the quality of fusion can be poor at best.

Secondly, as mentioned above, the size of the cage is an important issue. The future of spine surgery will be based upon minimally invasive surgical techniques as discussed above. The surgeon implants the cage or cages into the disc by use of a cannula. This allows for small skin incision to minimize soft tissue trauma and reduce recovery time and hospital stay. To properly relieve the pressure on the nerves and spinal cord, the collapsed disc space should be open to as close as possible to its precollapsed stage. With the present cage designs discussed above, the cage is designed to open the disc space to 16 mm, such cage requiring a cannula of 18 to 20 mm. Such a cannula requires a large incision. It would be desirable to provide a means to allow a 16 mm cage to go down a smaller cannula, such as a 12 mm or 14 mm cannula.

It is further desirable to allow the cage to share the stress with the surrounding bone. Such a dynamic would allow the cage to act not only as a required spacer, but also allow the bone to be stressed to improve fusion success and fusion quality.

It would further be desirable to provide the surgeon with a means of easily opening the disc space. Present day devices require instrumentation to open the disc space, which is often ineffective or difficult to do.

SUMMARY OF THE INVENTION

In accordance with the present invention there is provided a fusion implant for insertion between opposing vertebrae. The implant includes a body having an inner surface defining a hollow inner chamber for containing a graft material therein. The body further includes stress transfer means for transferring stress from the vertebrae surrounding the implant to the graft material within the implant.

The present invention further provides for the fusion implant to include a body portion consisting of a hollow shell having a central longitudinal axis. The shell includes at least one flexible body portion for allowing contraction and expansion about the axis.

The present invention further provides a method of implanting the fusion implant between opposing vertebrae by inserting the implant into a collapsed disc space between adjacent vertebrae, the implant including a collapsed body. The body is then expanded to spread the adjacent vertebrae apart.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE DRAWINGS

Figure 1:
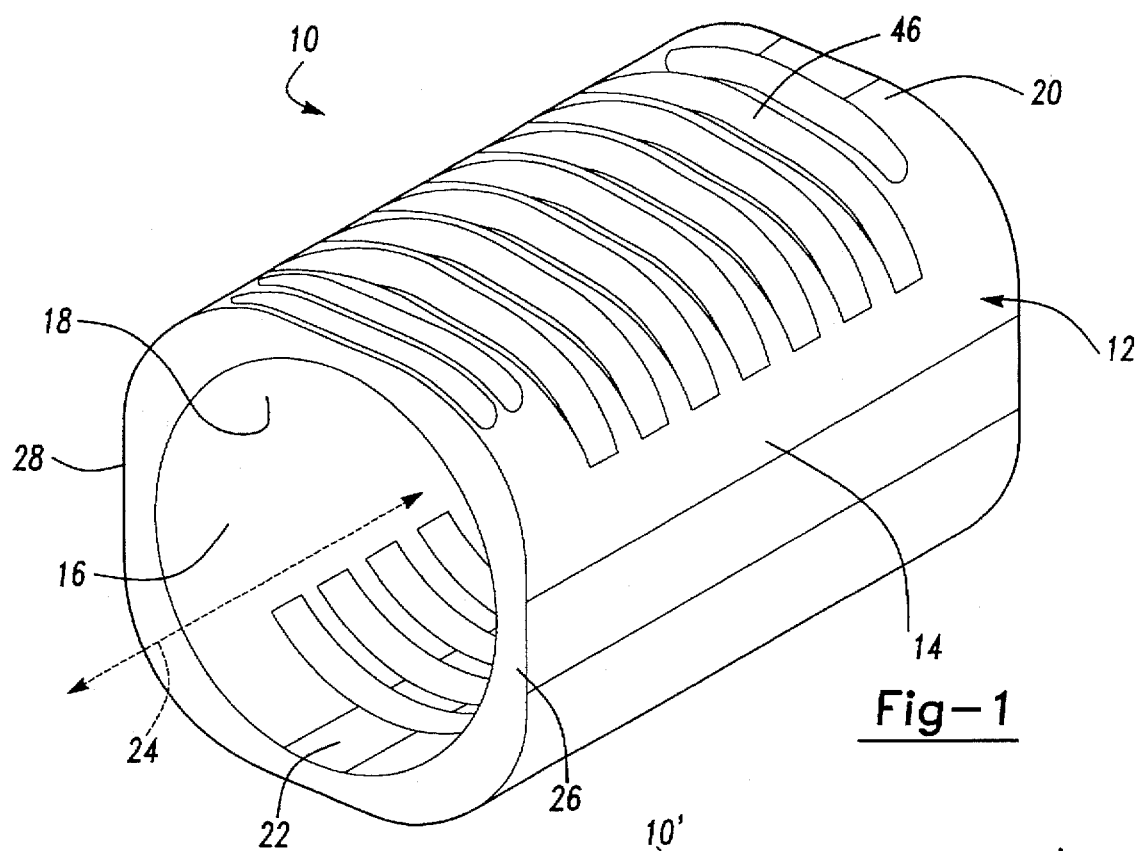
FIG. 1 is a perspective view of a fusion implant cage made in accordance with the present invention.

A fusion implant for insertion between opposing vertebrae is generally shown at 10 in the drawings. The several embodiments of the present invention are shown by primed numbers indicating like parts between the several embodiments.

Generally, the implant 10 includes a body portion Generally indicated at 12. The body portion 12 can be manufactured from various materials, such as composite materials of either two or more metals, plastics, or other materials well known in the art. Such devices can be either machined or molded, depending upon the material from which the implant 10 is made. For example, the implant 10 can be made from a metal material having spring like qualities as discussed below. The metal can be formed and then machined to shapes and tolerances described below. Alternatively, the body 12 can be made from a plastic material or composite which can be molded into the desired shape.

The body 12 includes an outer surface 14 and an inner surface 16. The inner surface 16 defines a hollow inner chamber 18 for containing a graft material (not shown) therein. Such general shapes of cages are well known in the art. Such shapes are exemplified by the '104, '602, and '308 patents discussed above.

The outer surface 14 can include a porous coating, as is known in the art, for allowing bone growth. The outer surface 14 can also be otherwise textured to enhance bone fixation.

In order to maximize chances for fusion to occur, various materials have been used to fill the insides of cages. Each material is chosen based on availability and to provide the best chance of good fusion. These include autograft or material taken from the patient during the surgery, allograft, which is bone removed from another patient, as well as processed allograft, which may be in small pieces and treated in a variety of ways. With the desire to decrease fusion time, biologically active materials may be used instead. These include bone treated with morphogenic proteins, calcium sulfate, and other artificial bone substitutes.

A characterizing feature of the present invention is that the body 12 includes stress transfer means for transferring stress from the vertebrae surrounding the implant 10 to the graft material contained within the implant 10. That is, unlike the rigid cages of the prior art which merely act as spacers, the present invention provides a cage body construction which shares the load with surrounding vertebrae. This is accomplished by a flexing of at least a portion of the body 12 in response to stress applied by surrounding vertebrae. Thus, the stress transfer means of the present invention includes at least one flexible portion of the body 12 which can deflect or otherwise transfer stress applied by the surrounding vertebrae to the contained graft material within the hollow inner chamber 18.

A first embodiment of the stress transfer means of the present invention is shown in FIG. 1. The body 12 includes an upper portion 20 and a lower portion 22 for contacting upper and lower vertebral end plates adjacent thereto after placement of the device. The upper and lower portions 20,22 are deflectable and therefore transfer stress from the adjacent vertebrae bodies to graft material contained within the hollow chamber 18. The upper and lower portions 20,22 act as spring like portions in an axial direction relative to a longitudinal axis 24 defined by the hollow inner chamber 18 to provide a means for outward flexation of the cage.

The body 12 can have a uniform thickness throughout or can have a varying thickness in at least one location. The body 12 can have relatively thinner side portions 26,28 which can be flexible relative to the remainder of the body 12. The body side portions 26,28 are shown as opposing body portions in FIG. 1. Such side body portions 26,28 can also deflect in response to stress applied to the body 12 by the surrounding vertebrae and thereby transfer such stress to the internal hollow chamber 18 and the graft material contained therein. Thus, the wall thickness can vary over the entire cage as desired.

The implant 10 of the present invention can be made so as to provide the practitioner with a series of implants having varied wall thicknesses thereby providing varied sizes and varied flexibility. The upper and lower portion 20,22 or the side portions 26,28 or a combination thereof can be calibrated to a patient's weight by varying the wall thickness chosen for the patient. Larger patients who would exert greater stresses upon an implant can be provided with implants 10 having thicker wall portions which remain flexible yet can withstand the loads applied. Likewise, patients having smaller body frames and carrying less weight can be provided with implants 10 having thinner body wall thicknesses to allow flexibility under lower stress conditions.

FIGS. 2 through 5 demonstrate various subspecies of the present invention wherein the body 12'-12"" includes a contractible body portion. More specifically, as shown in the embodiment in FIG. 2, the body 12' includes first and second open ends 30,32 defining the longitudinal axis 24' therebetween. A length of the body 12' extends about the longitudinal axis 24' and between the open ends 30,32. In this embodiment, the stress transfer means provides for contraction and expansion of the body 12 about the longitudinal axis 24 along the length thereof. Such contraction of the body 12 also provides for an implant 10 which could be contracted to a smaller size for delivery to a surgical site through a minimally sized cannula, as discussed in more detail below.

Figure 2:
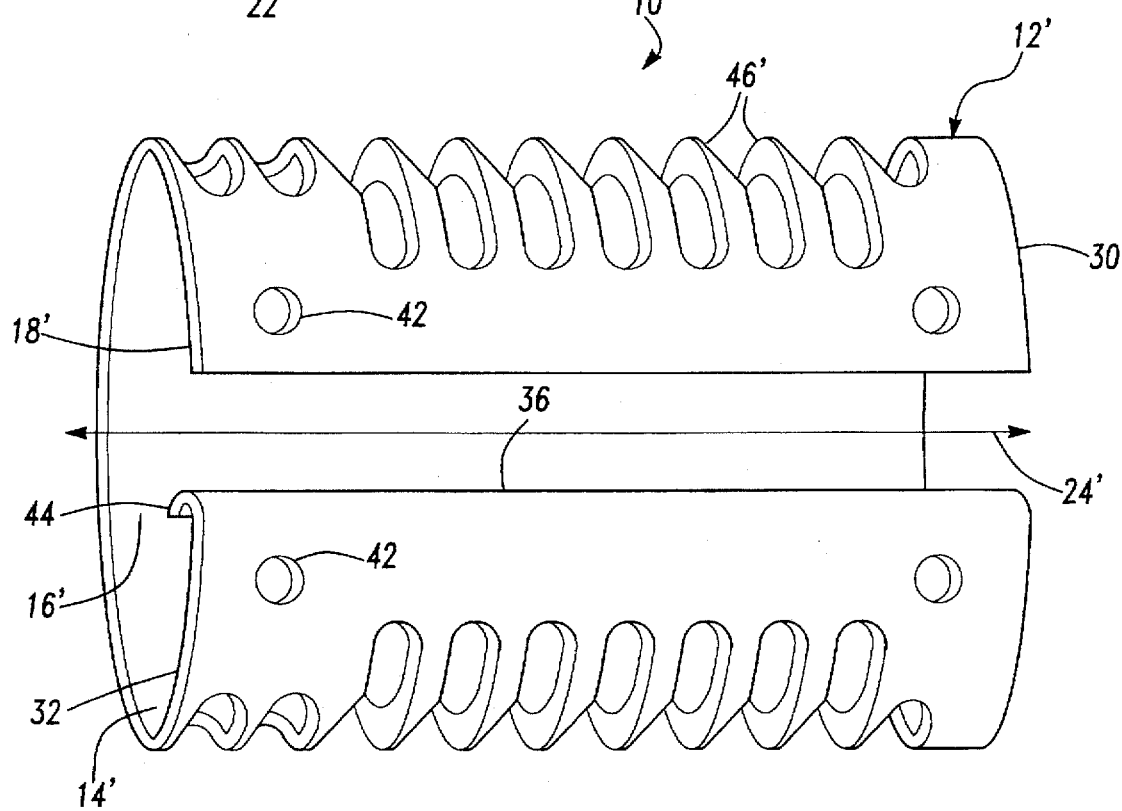
FIG. 2 is a perspective view of a second embodiment of the present invention.

Referring specifically to the structure shown in FIG. 2, the body 12', in its entirety, consists of a flexible material allowing for spring like contraction and expansion of the body 12' about the longitudinal axis 24'. Alternatively, a portion of the body 12' can be of a flexible material relative to the remainder of the body portion 12' as discussed above with regard to the first embodiment. What is critical is that at least a portion of the body 12' is flexible to allow for contraction and expansion of the body 12' about the longitudinal axis 24', as described below.

As stated above, such flexible materials are well known in the art, and can be spring like materials such as metal and metal composites, as well as plastic and plastic composites.

The body 12' includes opposing spaced edges 34,36 extending along the length of the body 12'. The combination of the flexible body 12' and substantially C-shaped cross section of the body 12' including the spaced edges 34,36 allows for the body 12' to be rolled within itself in a manner similar to a coiled piece of paper. The effective cross sectional diameter of the device can be easily contracted from 16 mm to as small as 8 or 10 mm. The implant can be inserted through as small as 12 mm or 14 mm cannula. This decrease in cross section diameter is quite significant in reducing the surgical wound from a size which would require scaring or plastic surgery to a size which would result in no scar.

The slot defined by the space between the edges 34,36 in combination with the shape of the body 12' can be varied in accordance with need. For example, in the embodiment shown in FIG. 2, the body 12' is of a cylindrical shape, the edges 34,36 being equal distance along their length thereby providing a straight slot. The straight slot provides for equal distance contraction of the cylindrical body 12' thereby maintaining the cylindrical body portion shape during contraction of the body 12' about the longitudinal axis 24'.

Figure 3:
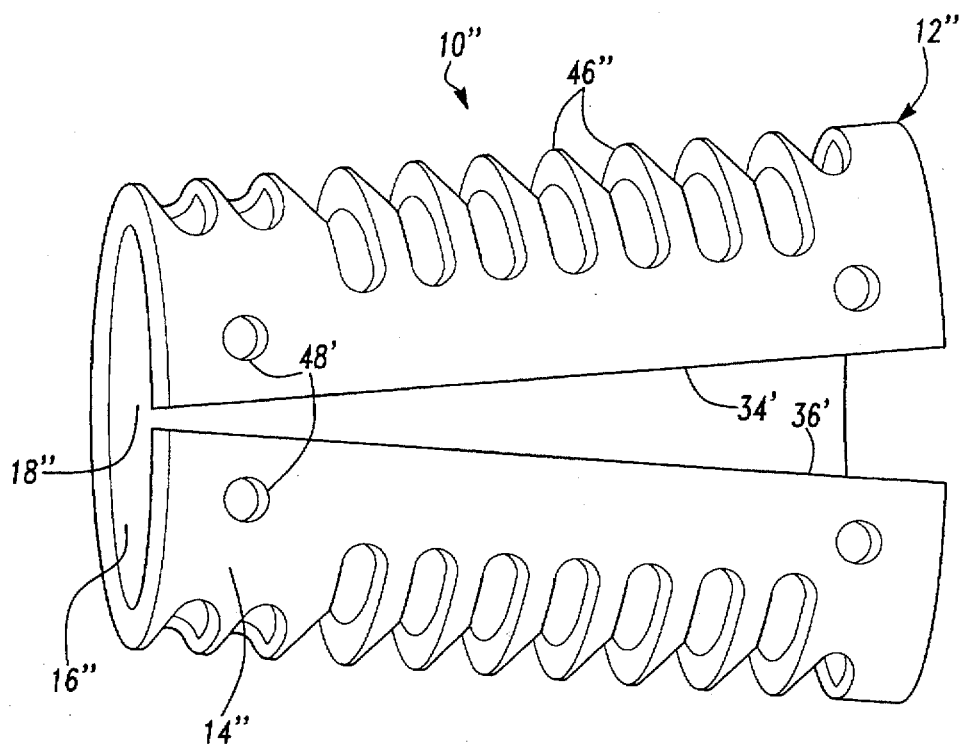
FIG. 3 is a perspective view of a third embodiment of the present invention.

An alternative construction is shown in FIG. 3 wherein the body portion 12" is of a conical shape. Conical shapes are preferred to restore nature spinal anatomy. That is, the natural spinal anatomy usually results in some angle in the space between the vertebrae, especially in the lower spine. The lower spine has the natural curve thereby resulting in disc spaces wherein the vertebral surfaces are not parallel to each other. A conical cage can restore the natural spinal anatomy by creating an angle between the opposing outer surfaces 14' of the body 12" which contact the vertebral end plates. The edges 34',36' diverge from each other along the length of the body 12". By collapsing the body 12" until the edges 34',36' touch, the conical cage becomes almost a cylinder, thereby being able to be inserted through a small cannula in a manner similar to the cylindrical cage shown in FIGS. 1 and 2.

Figure 4:
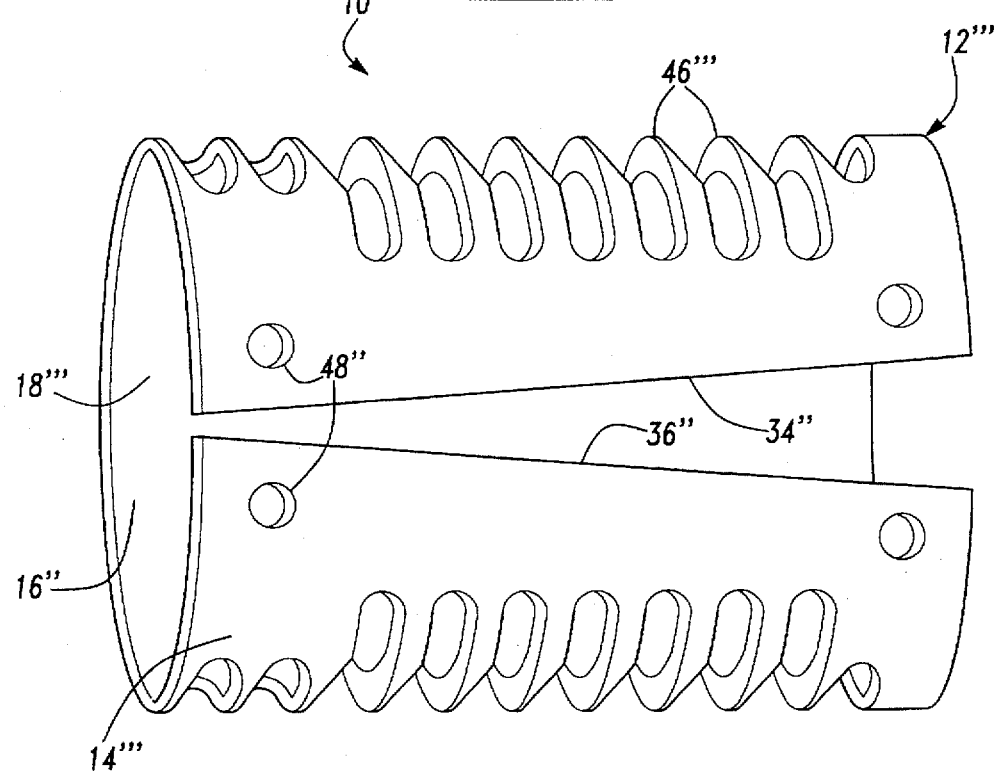
FIG. 4 is a perspective view of a fourth embodiment of the present invention.

A further embodiment of the present invention is shown in FIG. 4 wherein a cylindrical body portion 12'" is shown in combination with an angled slot 30 defined by edges 34",36". This embodiment exemplifies the variability of the present invention for use in various situations.

Figure 5:
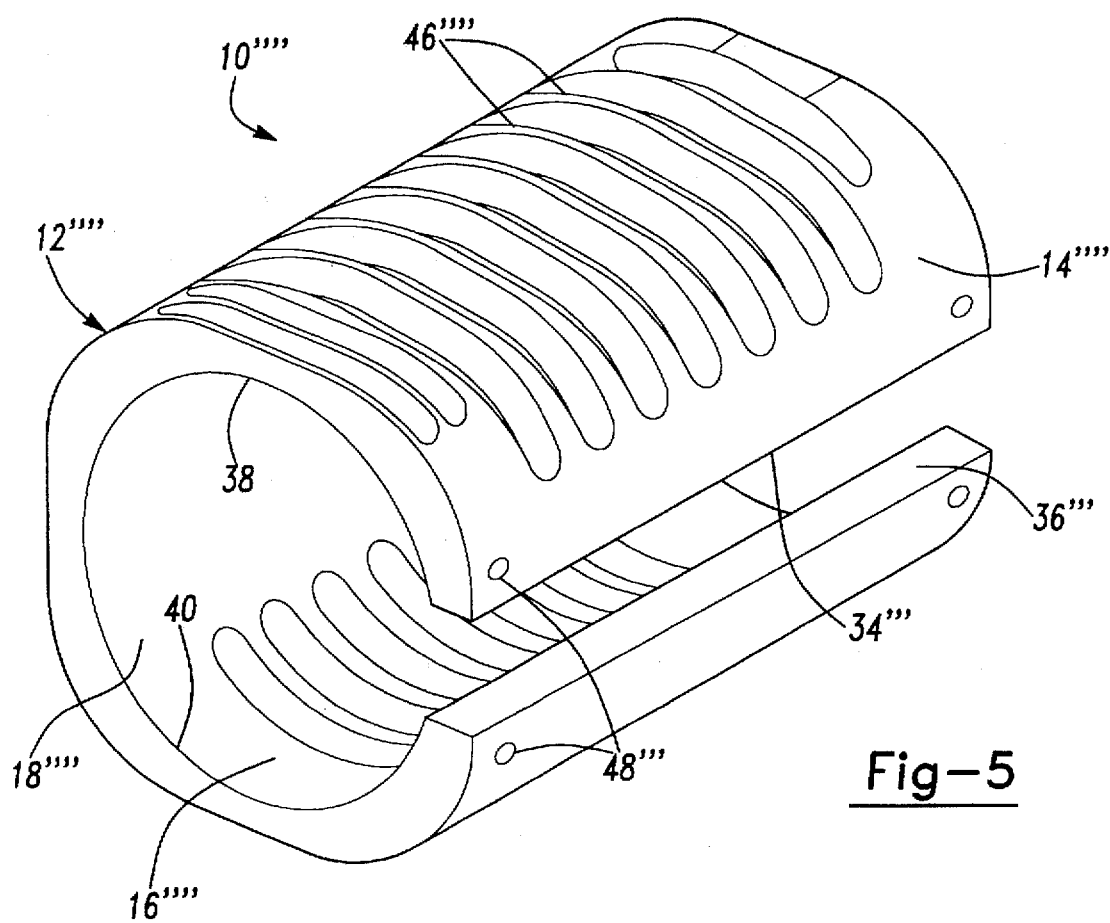
FIG. 5 is a perspective view of a fifth embodiment of the present invention.

Likewise, FIG. 5 shows a substantially cylindrically shaped body portion 14"" including parallel edges 34'",36'". However, the body portion 14"" includes substantially flat opposing side portion 38,40. This provides the body portion 14"" with a substantially rectangular shape. Such shapes are preferred to prevent rolling or rotation of the device within the disc space. The device 10"" can also be constructed in a more oblong shape thereby effectively filling the space that previously would have required two prior art devices. For example, U.S. Pat. 5,192,327 to Brantigan discloses oblong implants for vertebrae, requiring several implants to effectively produced a desired result. The present invention can utilize a single implant of varied shapes allowing for the implantation of a single implant instead of multiple implants.

As shown in FIG. 2, the body 12' can include a contraction limiting mechanism for limiting the contraction of the body 12' about the longitudinal axis 24'. The contraction limiting mechanism can include a lip portion 44 extending from one or both of the edges 34,36 (the lip being shown extending from edge 36 in FIG. 2). As shown in FIG. 2, edge 34 will contact and abut against the lip portion 44 during contraction of the body 12' about the longitudinal axis 24' thereby limiting the contraction of the body 12' about the longitudinal axis 24'.

The lip portion 44 also acts as a limiting mechanism for the amount of load that will be carried by the body 12' and transferred to the internally contained graft material. The amount of contraction of the body 12' about the longitudinal axis 24' in response to stress transferred from the surrounding vertebra end plates is controlled by the lip portion 44 as the lip portion 44 only allows the cage to load share to a certain point and then act as a spacer if the graft does not fully fuse or is of poor quality. In other words, stress will be transferred by the body 12' as the body contracts between the expanded space between edges 34,36 and the contracted state wherein the edges 34,36 either contact or the edge 34 contacts the lip 44. The lip 44 provides for a wider surface area for contact between the edges 34,36. Once sufficient stress is applied to the body 12' so that the edges 34,36 are in contact, then no more stress is transferred unless the body 12' includes further flexible portions as detailed with regard to the embodiment shown in FIG. 1. In this maximally contracted state, the body 12' only acts as a spacer, no longer transferring stress. However, the spacer at least maintains sufficient spacing to allow for protection of the adjacent nerve and spine portions.

Each of the bodies 12–12"" include means for fixing the implant 10–10"" between the opposing vertebrae. Each of the embodiments include toothed patterns in the form of threads 46 or teeth or the like. Such threads can be made in accordance with various shapes or designs as shown in the prior art. Such threads can be helical, straight, angled, or wedged shaped or various other shapes or designs well known in the art.

Each of the contractible embodiments of the present invention are shown with spaced holes 48, each pair of holes being disposed about the slot shown in FIGS. 2–5. The holes are made for engagement by an instrument (not shown) including tongs or the like which can be used to force the body 12'–12"" to the contracted state for insertion into the cannula. Likewise, a retaining plate (not shown) can be used when contraction and expansion are required for implantation and not desired for long term use. The attachment can be attached by grooves, threads, or teeth after cage insertion and expansion and provide support to the implant.

The present invention can be made from a memory metal such as Nitinol. Such metals can be bent to a desired shape, such as bending the body 12'–12"" into contracted shape and maintain the contracted shape. Once implanted, an instrument can be used to cause an electric current, heat or cold to be applied to the body thereby inducing the memory metal to return to its original expanded shape. Thusly, the implant can be inserted into a collapsed or substantially collapsed disc space between two vertebrae. The stimulus, such as heat, electric current, or cold can be applied to the implant whereby the implant will then return to its expanded shape thereby expanding the disc space to effectuate relief of the pinched nerves or the like. The implant will then maintain the spacing thereby effectuating relief to the patient.

In operation, if the implant is to be used by placement directly through an incision and without a cannula, the implant not requiring a slot might be used. The implant is disposed through an incision and retraction to the site at which the implant is to be disposed. Having made the appropriate incision and removed sufficient disc material to create a space for the cage or cages when two smaller cages are desired in place of a single cage, the implants are inserted into the space such that the teeth 46–46"" on the outer surface above the implant retain the implant 10–10"" in the appropriate position.

To utilize a smaller cannula and/or to utilize the ability of the implant to open up a disc space, an implant having a slot therein such as shown in FIGS. 2 through 5 is utilized. The implant is contracted and disposed into the cannula for placement in the disc space, as described above. Once, the insert escapes from the cannula and into the disc space, the implant either naturally springs to its original shape or is induced to its original shape by stimulus, if the implant is made from a memory material, as discussed above.

As with prior art devices, the implant contains a graft material for inducing fusion. By the ability of the implant to contract and expand, stress is applied by the vertebral end plates on the body 12–12"" of the implants 10–10"" is transferred to the graft material thereby transferring the load of the vertebral end plates to the contained graft material, the device takes advantage of and applies Wolf's law thereby providing excellent fusion quality.

In view of the above, the present invention provides an implant which can either be used solely as a spacer which transfers stresses from the adjoining vertebral end plates to the graft contained within the implants or also as a contractible and expandable implant.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

What is claimed is:

1. A fusion implant for insertion between opposing vertebrae, said implant comprising: a body including an inner surface defining a hollow inner chamber for containing a graft material therein, said body including stress transfer means for transferring stress from the vertebrae surrounding said implant to the graft material contained within said implant.

2. An implant as set forth in claim 1 including upper and lower portions for contacting upper and lower vertebrae bodies, said upper and lower portions being deflectable and defining said stress transfer means.

3. An implant as set forth in claim 2 wherein said body is of uniform thickness.

4. An implant as set forth in claim 2 wherein said body varies in thickness in at least one location.

5. An implant as set forth in claim 1 wherein said body includes first and second open ends defining a longitudinal axis therebetween and a length of said body extending about said longitudinal axis and between said open ends, said stress transfer means providing for contraction and expansion of said body about said longitudinal axis along said length thereof.

6. An implant as set forth in claim 5 wherein said body consists of a flexible material allowing for spring like contraction and expansion of said body about said longitudinal axis.

7. An implant as set forth in claim 6 wherein said body includes opposing spaced edges extending along said length of said body.

8. An implant as set forth in claim 7 wherein said spaced edges are spaced an equal distance apart along said length of said body.

9. An implant as set forth in claim 8 wherein said body is cylindrical.

10. An implant as set forth in claim 7 wherein said spaced edges diverge from each other along said length of said body.

11. An implant as set forth in claim 10 wherein said body is conical.

12. An implant as set forth in claim 7 further including contraction limiting means for limiting the contraction of said body about said longitudinal axis.

13. An implant as set forth in claim 12 wherein at least one of said edges includes a lip portion extending therefrom, said other of said edges contacting and abutting against said lip portion during contraction of said body about said longitudinal axis thereby limiting the contraction of said body about said longitudinal axis.

14. An implant as set forth in claim 5 wherein said body consists of a memory metal which is bendable from an original state to a contracted state and returns to said original state upon application of a stimulus.

15. An implant as set forth in claim 1 wherein said body includes fixation means for fixing said implant to the opposing vertebrae.

16. An implant as set forth in claim 15 wherein said fixation means includes threaded portions on opposed outer surfaces of said body, said body including opposing flexible side walls in between said threaded portions defining said stress transfer means.

17. An implant as set forth in claim 1 wherein said body is collapsible and expandable whereby said body automatically expands upon release from an insertion instrument to widen a disc space between opposing vertebral end plates.

18. An implant as set forth in claim 1 including an external surface of said body, said external surface including a porous coating for allowing bone ingrowth.

19. An implant as set forth in claim 1 including a textured external surface for enhancing bone fixation.

20. An implant for insertion between opposing vertebrae, said implant comprising: a body consisting of a hollow shell having a central longitudinal axis, said shell including at least one flexible body portion for allowing contraction and expansion about said axis, wherein said body consists of a flexible material allowing for spring-like contraction and expansion of said body about said longitudinal axis.

21. An implant as set forth in claim 20 wherein said body includes opposing spaced edges extending along said length of said body.

22. An implant as set forth in claim 20 wherein an area of said body includes openings therethrough for allowing graft material inside said body to contact bone outside of said body upon insertion of said implant.

23. An implant for insertion between opposing vertebrae, said implant comprising: a body consisting of a hollow shell having a central longitudinal axis, said shell including at least one flexible body portion for allowing contraction and expansion about said axis, wherein said body is collapsible and expandable whereby said body automatically expands upon release from an insertion instrument to widen a disc space between opposing vertebral end plates.

24. An implant as set forth in claim 20 including an external surface of said body, said external service including a porous coating for allowing bone growth.

25. An implant as set forth in claim 20 including a textured surface for enhancing bone fixation.

* * * * *